United States Patent
Zhang et al.

(10) Patent No.: US 7,479,111 B2
(45) Date of Patent: Jan. 20, 2009

(54) METHODS FOR MEASURING BLOOD PRESSURE WITH AUTOMATIC COMPENSATIONS

(75) Inventors: Yuan Ting Zhang, Hong Kong (HK); Lung Yip, Hong Kong (HK); Xiao Fei Teng, Harbin (CN); Chung Yan Carmen Poon, Hong Kong (HK); Chi Man Lee, Hong Kong (HK)

(73) Assignee: The Chinese University of Hong Kong, Hong Kong (CN)

( * ) Notice: Subject to any disclaimer, the term of this patent is extended or adjusted under 35 U.S.C. 154(b) by 620 days.

(21) Appl. No.: 11/134,637

(22) Filed: May 20, 2005

(65) Prior Publication Data

US 2005/0261593 A1   Nov. 24, 2005

(30) Foreign Application Priority Data

May 20, 2004   (CN) .................. 2004 1 0042522

(51) Int. Cl.
    A61B 5/02   (2006.01)
(52) U.S. Cl. ...................... 600/485; 600/481
(58) Field of Classification Search ............ 600/481, 600/485
    See application file for complete search history.

(56) References Cited

U.S. PATENT DOCUMENTS

| 5,649,543 | A  | * | 7/1997  | Hosaka et al. ............. 600/493 |
| 6,027,455 | A  | * | 2/2000  | Inukai et al. ............... 600/490 |
| 6,036,652 | A  | * | 3/2000  | Inukai et al. ............... 600/493 |
| 6,647,287 | B1 | * | 11/2003 | Peel et al. .................. 600/513 |
| 2002/0055672 | A1 | * | 5/2002 | Zhang ....................... 600/322 |
| 2004/0030261 | A1 | * | 2/2004 | Rantala ..................... 600/561 |
| 2004/0267103 | A1 | * | 12/2004 | Li et al. ..................... 600/323 |
| 2005/0096557 | A1 | * | 5/2005 | Vosburgh et al. .......... 600/509 |
| 2005/0154299 | A1 | * | 7/2005 | Hoctor et al. .............. 600/437 |

OTHER PUBLICATIONS

B. Gribbin, A. Steptoe, and P. Sleight, "Pulse Wave Velocity as a Measure of Blood Pressure Change", Psychophysiology, vol. 13, No. 1, pp. 86-90, 1976.
J. Woo, "Nutrition and health issues in the general Hong Kong population", HKMJ, vol. 4, No. 4, 1998, pp. 383-388.
"Electronic or automated sphygmomanometers", ANSI/AAMI, SP10, 1992.
Messrs J.C. Bramwell and A.V. Hill, "The Velocity of the Pulse Wave in Man", Proceedings of the Royal Society, London, pp. 298-306 (1922).
Norman M. Kaplan, "Clinical Hypertension", Williams & Wilkins, Sixth Edition, Table of Contents (1994).

* cited by examiner

*Primary Examiner*—Robert L Nasser
*Assistant Examiner*—Karen E Toth
(74) *Attorney, Agent, or Firm*—Katherine M. Kowalchyk; Merchant & Gould P.C.

(57) ABSTRACT

Disclosed is a method for measuring an arterial blood pressure of a subject comprising detecting a pulse-wave-related signal of the subject; extracting a feature from the signals; determining a factor that can affect the arterial blood pressure of the subject; and determining the arterial blood pressure based on the feature with an automatic compensation for the factors. The disclosed method reduces the error in measuring the blood pressure based on characteristics of the pulse-wave-related signals.

24 Claims, 9 Drawing Sheets

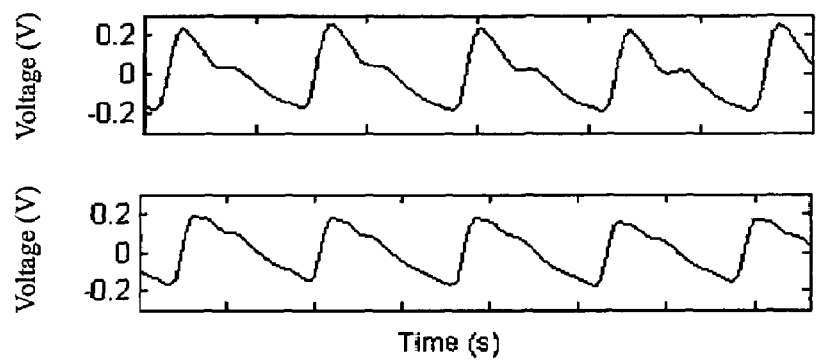
Fig. 9 Photoplethysmographic Signals in (a) warm and (b) cool conditions.
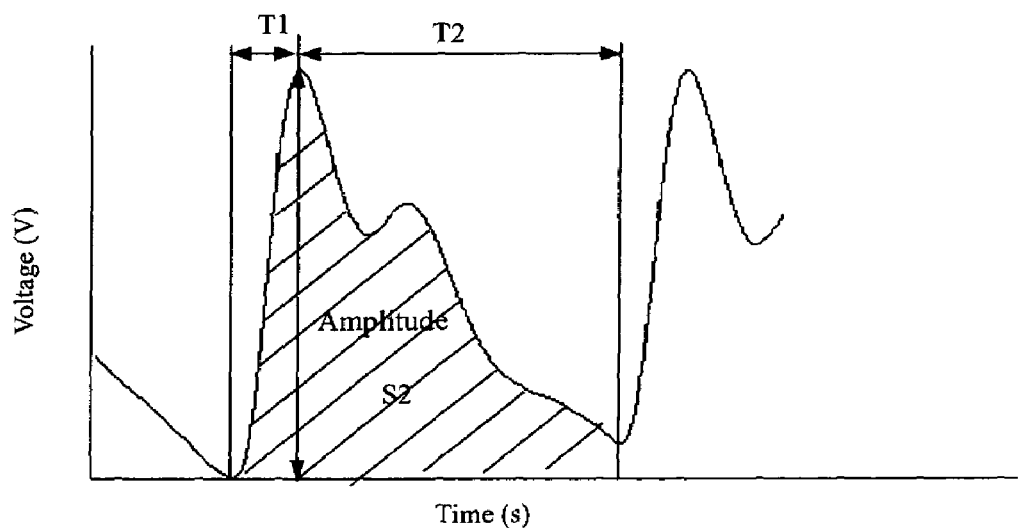
Fig. 10

METHODS FOR MEASURING BLOOD PRESSURE WITH AUTOMATIC COMPENSATIONS

CROSS REFERENCE OF RELATED APPLICATIONS

The present application claims the benefit of Chinese application No. 2004100425224 filed on May 20, 2004, entitled method for continuously cuffless-measuring blood pressure with automatic compensations, which is explicitly incorporated herein by reference in its entirety.

FIELD OF THE INVENTION

The invention generally relates to a method for measuring arterial blood pressure of human, particularly to a method for measuring arterial blood pressure based on a pulse transit time of human with an automatic compensation.

BACKGROUND OF THE INVENTION

Measuring blood pressure is a basic way of monitoring and diagnosing human health, and especially important for elderly people suffering from cardiovascular diseases.

Blood pressure of human can be measured invasively or non-invasively. The invasive measurement is a direct way to measure blood pressure. A catheter should be provided which is inserted into the artery of human during the measurement. The method requires professional medical staff to operate. It is costly, and bears the risk of viral infection.

Noninvasive measurement is an indirect way to measure blood pressure. Because the method is safe, convenient, and comfortable to users, it is now widely used in the hospitals. The method is also often used by patients who would like to monitor their blood pressure at home. As people have become more aware of the threat of hypertension and the importance of early treatment, the demand for noninvasive blood pressure meters is on the rise.

The common noninvasive measurement techniques can be classified into the auscultative technique, oscillometric technique, the method of tonometry and the method by measurement of pulse transit time.

The auscultative technique is usually used with a mercury sphygmomanometer. The basic components in the mercury sphygmomanometer include an inflatable cuff and a mercury barometer. In some of the newer products, the mercury barometer is replaced by an electronic pressure sensor. Nonetheless, the working principle remains the same.

Arterial blood pressure is to be measured on the upper arm of a person. Air in the cuff is first released, and then the cuff is wrapped around an upper limb. A stethoscope is need for the detection of the Korotkoff sounds. The head of the stethoscope is placed over the brachial artery. Air is pumped into the cuff until the level of mercury in the barometer reaches a predetermined threshold. The Korotkoff sounds are to be detected while the cuff is being slowly deflated. The cuff pressures at which the first and the fifth Korotkoff sounds are detected represent the systolic BP (SBP) and diastolic BP (DBP) of the subject respectively.

Although this method can be used to identify the systolic and the diastolic blood pressure, it is not suitable for measuring the blood pressure of those people with weaker 5th Korotkoff sounds.

The oscillometric technique can overcome the shortcoming of the auscultative technique in the way that it can measure blood pressure of those who have weak Korotkoff sounds. However, the technique also requires an inflatable cuff to be wrapped around the upper limb of the subject. While the inflated cuff is slowly deflated, the pressure in the cuff oscillates as a result of arterial pulsation. From the pattern of oscillation, the mean blood pressure, systolic blood pressure and diastolic blood pressure are determined. Mean blood pressure is the cuff pressure at which the maximum amplitude of oscillation is detected. Systolic blood pressure and diastolic blood pressure are estimated from the mean blood pressure and the oscillation pattern. For example, systolic blood pressure is typically the cuff pressure before the oscillation reaches the maximum amplitude and at which the amplitude of oscillation equals to a given percentage of the maximum amplitude. Similarly, diastolic blood pressure is typically the cuff pressure where the oscillation has passed the maximum amplitude and at which the amplitude of oscillation equals to a given percentage of the maximum amplitude. It is clear that systolic and diastolic blood pressure depends on the predetermined percentages.

Most of the noninvasive blood pressure meters currently available on the market are based on the auscultative or oscillometric technique. Both of these methods require the inflation and deflation of the cuff. Therefore, they are not suitable for frequent and continuous measurement of blood pressure.

The principle of the tonometers is to gently press a vessel against the underlying bone in order to counteract the circumferential stress at the vessel wall. There should be an external pressure at which the internal and external pressures of the vessel are thereby equalized and the external pressure is modulated such that the equalization is maintained. The applied pressures are recorded by an array of sensors positioned on the surface of the artery, to thereby determine the blood pressure. The accuracy of the measurement is readily affected by positions and angles of the sensors.

Blood pressure can also be estimated from pulse transit time. Arterial blood pressure is found to be inversely proportional to the velocity of the pulse wave. This theory has been disclosed in some papers: Messrs J. C. Bramwell and A. V. Hill, "The Velocity of the Pulse Wave in Man", Proceedings of the Royal Society, London, pp. 298-306, 1922; and B. Gribbin, A. Steptoe, and P. Sleight, "Pulse Wave Velocity as a Measure of Blood Pressure Change", Psychophysiology, Vol. 13, No. 1, pp. 86-90, 1976, which are incorporated herein as reference.

A blood pressure meter that measure blood pressure by pulse transit time often uses an optical sensor to collect a photoplethysmographic signal from the tip of fingers. The meter is of a simple construct with a small size, and low cost. It also provides a way to measure arterial blood pressure continuously for a long period of time.

A meter based on the pulse transit time requires calibrating itself by a conventional blood pressure meter before it is used. The calibration process is there to establish a relationship between a blood pressure on an upper limb and a pulse transit time. The absolute blood pressure is then determined according to the predetermined relationship based on a pulse transit time obtained from the measurement.

However, the pulse transit time is often influenced by a lot of factors other than blood pressure, such as the temperature of the fingers and the contacting force of the fingers acting on the sensor. Meanwhile, blood pressure is also affected by other physiological variables that are not reflected in the pulse transit time, for example, sympathetic nervous activity and cardiac output. Therefore, in order to reduce errors of the blood pressure measurement by pulse transit time described in prior art, it is necessary to develop a new method, which is not only based on the pulse transit time, but also includes a compensation for other factors that affect the measurement.

Other sources about the blood pressure measurement may be referred to: Norman M. Kaplan, "Clinical Hypertension"; J Woo, "Nutrition and health issues in the general Hong Kong population", HKMJ, Vol. 4, No 4, 1998, pp383-388; and "Non-invasive blood pressure", ANSI/AAMI, SP10, 1992, which are incorporated herein as reference.

SUMMARY OF THE INVENTION

The invention aims to provide a method for measuring blood pressure on the basis of the pulse transit time in view of an automatic compensation scheme that counterbalances the effect of other factors mentioned above, to hereby overcome the technical drawbacks in prior art.

The method of the invention for measuring an arterial blood pressure of a subject comprises:
 a) detecting a pulse-wave-related signal of the subject;
 b) extracting a feature from the signals;
 c) determining a factor that can affect the feature; and
 d) determining the arterial blood pressure based on the feature with an automatic compensation for the factor.

According to a preferred embodiment of the invention, a feature extracted from the signals is a pulse transit time. In other embodiments of the invention, a feature can be a characteristic time interval of the pulse-wave-related signal, such as a rising time and a falling time.

The pulse-wave-related signal according to the invention is selected from a photoplethysmogram, a pressure wave signal, a blood flow signal, a bioelectrical signal, and a bioacoustic signal.

In step b) of the invention, the pulse transit time is determined by a time interval between a first characteristic point at the bioelectrical signal and a second characteristic point at the pulse-wave-related signal. Preferably, the bioelectrical signal comprises an electrocardiogram, and the bioacoustic signal comprises a phonocardiogram.

In an embodiment of the present invention, the pulse-wave-related signal and the bioelectrical signal are detected by a sensor disposed at the subject.

According to another preferred embodiment of the invention, the factor in step c) includes a contacting force that the subject acts on the sensor for measuring the pulse transit time, an ambient temperature, and nervous activities and/or cardiac output.

In preferred embodiments of the invention, the pulse-wave-related signal is photoplethysmogram, and the characteristic point is selected from one of the peak, the foot, and a point at 10% or 50% amplitude of the photoplethysmographic signal.

The characteristic point on the bioelectrical signal may be selected from a point on an R wave of the electrocardiogram and preferably from the peak of the R wave.

The pulse transit time may be determined by a time interval between the second characteristic point on the photoplethysmogram and the first characteristic point on the electrocardiogram within a cardiac cycle.

In a further preferred embodiment of the invention, the step d) comprises: obtaining coefficients from a calibration process; counterbalancing the effect of the contacting force on the pulse transit time with a first compensation term; determining an estimated value of the blood pressure from the corrected pulse transit time; counterbalancing the effect of nervous activities and/or cardiac output on the estimated value of the blood pressure with a second compensation term; and counterbalancing the effect of an ambient temperature on the estimated value of the blood pressure with a third compensation term to obtain the blood pressure.

In step d), counterbalancing the effect of the nervous activities and/or cardiac output on the estimated value of the blood pressure can be taken in the form of a linear function, a nonlinear function, or other mathematically equivalent functions.

In some particular embodiments of the invention, one of the following equations is employed to determine the blood pressure:

$$Psys=As/(Ts+Tcs)^{n1}+Bs+Cs^{\alpha1}+Ds^{\beta1}$$

$$Pdia=Ad/(Td+Tcd)^{n2}+Bd+Cd^{\alpha2}+Dd^{\beta2}, \text{ or}$$

$$Psys=As'\times\ln(Ts+Tcs)^{n1}+Bs'+Cs^{\alpha1}+Ds^{\beta1}$$

$$Pdia=Ad'\times\ln(Td+Tcd)^{n2}+Bd'+Cd^{\alpha2}+Dd^{\beta2}, \text{ or}$$

$$Psys=As''\times Cs^{\alpha1}\times Ds^{\beta1}/(Ts\times Tcs)^{n1}+Bs''$$

$$Pdia=Ad''\times Cd^{\alpha2}\times Dd^{\beta2}/(Td\times Tcd)^{n2}+Bd''.$$

In the above equations, Psys and Pdia are a systolic pressure blood (SBP) and a diastolic blood pressure (DBP), respectively; Ts and Td are a pulse transit time to determine the systolic and diastolic blood pressure respectively. As, Bs, Ad, Bd, As', Bs', Ad', Bd', As'', Bs'', Ad'', and Bd'' are pre-defined constants or user-dependent coefficients that are obtained from a calibration process.

The calibration process described in the invention may generally comprise: obtaining a reference blood pressure (SBP and DBP) of a subject by a conventional blood pressure measurement technique; measuring a pulse transit time (Ts and Td) corresponding to the reference blood pressure; and determining coefficients As, Bs, Ad and Bd from the reference blood pressure and the pulse transit time.

Tcs and Tcd, as a first compensation term, are used to counterbalance the effect of the contacting force on the pulse transit times Ts and Td, respectively. The corrected pulse transit times are each raised to powers n1 and n2, where $0<n1,n2\leq3$. Cs and Cd, as a second compensation term, are used to counterbalance the effect of nervous activities and/or cardiac output on the measurement of the systolic and diastolic blood pressure, respectively. Cs and Cd are each raised to powers $\alpha1$ and $\alpha2$, where $0\leq\alpha1,\alpha2\leq2$. Ds and Dd, as a third compensation term, are used to counterbalance the effect of an ambient temperature on the measurement of the systolic and diastolic blood pressure, respectively. Ds and Dd are each raised to powers $\beta1$ and $\beta2$, where $0\leq\beta1,\beta2\leq2$.

The compensation terms defined herein can be determined by characteristics of the pulse-wave-related signal.

In the invention, photoplethysmogram is preferably used as a pulse-wave-related signal. As a result, each of the compensation terms is determined by at least one photoplethysmographic signal characteristic, at least one calibration constant, and at least one weighting factor.

The photoplethysmographic signal characteristic includes but not limited to: a magnitude, a characteristic time interval, and a pulse area of the photoplethysmogram and/or of a higher order moment or a higher order derivative of the photoplethysmogram.

In an embodiment of the present invention, the first compensation term, Tcs and Tcd, is determined by a magnitude of photoplethysmogram, a first calibration constant and a first weighting factor.

In one embodiment of the invention, the first calibration constant is determined by the magnitude of the photoplethysmogram obtained at a different contacting force during the calibration.

The first weighting factor may be determined by a ratio of a change in the pulse transit time to a change in the blood pressure during the calibration.

The second compensation term, Cs and Cd, based on the nervous activities and/or cardiac output may be determined by a characteristic time interval of the photoplethysmogram, a second calibration constant and a second weighting factor.

The characteristic time interval defined herein may include a time interval from the foot of the photoplethysmogram to a characteristic point at a peak of the photoplethysmogram within a cardiac cycle, or a time interval from the peak of the photoplethysmogram to a characteristic point at a foot of the photoplethysmogram at the next cardiac cycle.

In an embodiment of the present invention, the second weighting factor is determined by a characteristic time interval of the photoplethysmogram and a percentage difference in the characteristic time interval obtained during the measurement of the blood pressure as compared to that obtained during the calibration.

The percentage difference is obtained by the following equations:

$$\% \text{ Diff.} = \frac{\text{Char. Time Interval}|_{during\ estimation} - \text{Char. Time Interval}|_{during\ calibration}}{\text{Char. Time Interval}|_{during\ calibration}}, \text{ or,}$$

$$\% \text{ Diff.} = \frac{\text{Char. Time Interval}|_{during\ calibration}}{\text{Char. Time Interval}|_{during\ estimation} - \text{Char. Time Interval}|_{during\ calibration}}.$$

In the invention, the second calibration constant in the compensation term can be obtained from a ratio of As to Bs for the estimation of the systolic blood pressure, and that of Ad to Bd for the estimation of the diastolic blood pressure.

The third compensation term, Ds and Dd, based on the ambient temperature is determined by a pulse area of a photoplethysmogram-related characteristic and a third weighting factor. An example of the pulse area is a normalized pulse area or a normalized falling area of the photoplethysmogram. In the invention, the third weighting factor can be a constant ranging from 10 to 100.

Preferably, the pulse transit times Ts and Td that are used in the calibration or measurement process are obtained by averaging P individual pulse transit times, i.e.:

$$Ts = \frac{1}{P}\sum_{i=1}^{P} Ts_i, \text{ and, } Td = \frac{1}{P}\sum_{i=1}^{P} Td_i$$

where i is the index of a series of pulse transit times and $1 \leq i \leq P$.

The difference between the average pulse transit times Ts and Td and each individual pulse transit time $Ts_i$ and $Td_i$ must be within a boundary, that is, $Th\_\text{Errlow} < Ts - \{Ts_i\} < Th\_\text{Errhigh}$, and, $Th\_\text{Errlow} < Td - \{Td_i\} < Th\_\text{Errhigh}$.

By introducing the compensation terms for counterbalancing the effect of the contacting force, the nervous activities and/or cardiac output, and the ambient temperature, the invention reduces the error in measuring the blood pressure based on characteristics of the pulse-wave-related signals. The invention utilizes the characteristic of the photoplethysmogram itself for the compensation, and does not require extra sensors. Therefore, it has the advantages of cost effective, miniature and user-friendly.

BRIEF DESCRIPTION OF THE DRAWINGS

FIG. 9 illustrates photoplethysmogram waveforms obtained at different ambient temperatures; and FIG. 10 illustrates the pulse area of the photoplethysmogram-related characteristics.

DETAILED DESCRIPTION OF THE PREFERRED EMBODIMENTS

The present invention will be described in detail with reference to the drawings.

In the present invention, the term "photoplethysmogram" has the same meaning as photoplethysmograhic signal, unless otherwise specified.

Figure 1:
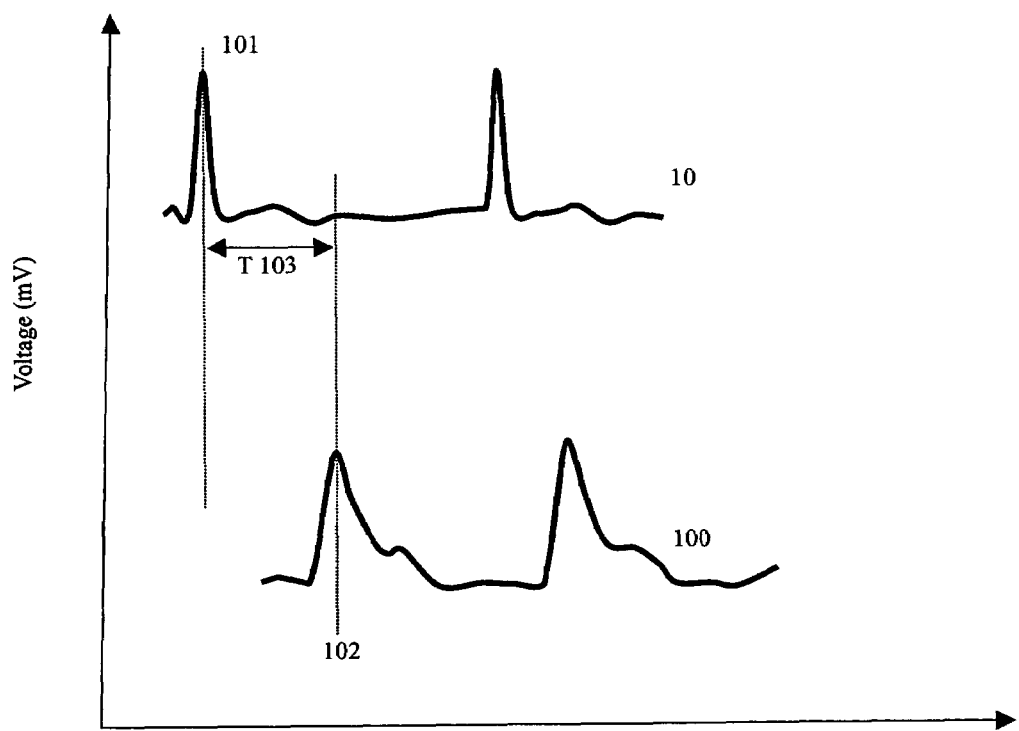
FIG. 1 shows a photoplethysmogram and an electrocardiogram from a subject, where a pulse transit time in an embodiment of the invention is determined.

Referring to FIG. 1, a transit time of a pulse wave according to an embodiment of the invention is shown. In this embodiment, the pulse transit time is determined from an electrocardiogram (ECG) and a photoplethysmogram (PPG) of a subject.

As shown in FIG. 1, numeral references 10 and 100 respectively represent an electrocardiogram (ECG) and a photoplethysmogram (PPG) obtained from a subject at a time interval. Numeral references 101 and 102 represents a time where the ECG and PPG reach a peak respectively at a predetermined interval. In this embodiment, the time 101 when the ECG reaches the peak is considered as a characteristic point, and the time 102 when the PPG signal reaches the peak is also considered as a characteristic point. A time difference T103 between 102 and 101 is considered as a pulse transit time.

In other embodiments, other points at the electrocardiogram 10 such as at the bottom (trough) and at a point of 50% amplitude may be considered as a characteristic point of the electrocardiogram 10. In this case, a point at the photoplethysmogram 100 corresponding to the selected point at the electrocardiogram 10 should be chosen as a characteristic point of the photoplethysmogram 100.

The time interval T103 is considered as a pulse transit time of both Ts and Td to estimate the systolic and diastolic blood pressure respectively, which will be further described below. Ts and Td can be designated the same or different depending on the election of the characteristic points on the photoplethysmogram.

It should be appreciated for those skilled in the art that the determination of the pulse transit time is not limited to the method described above. For example, other pulse-waverelated signals such as a pressure wave signal, a blood flow signal and a phonocardiogram of a subject can be used in replace of the photoplethysmogram. In that case, for example, the pulse transit time Ts and Td can be determined by a time interval from a characteristic point on electrocardiogram to a characteristic point on any of the selected pulse-wave-related signals.

Figure 3:
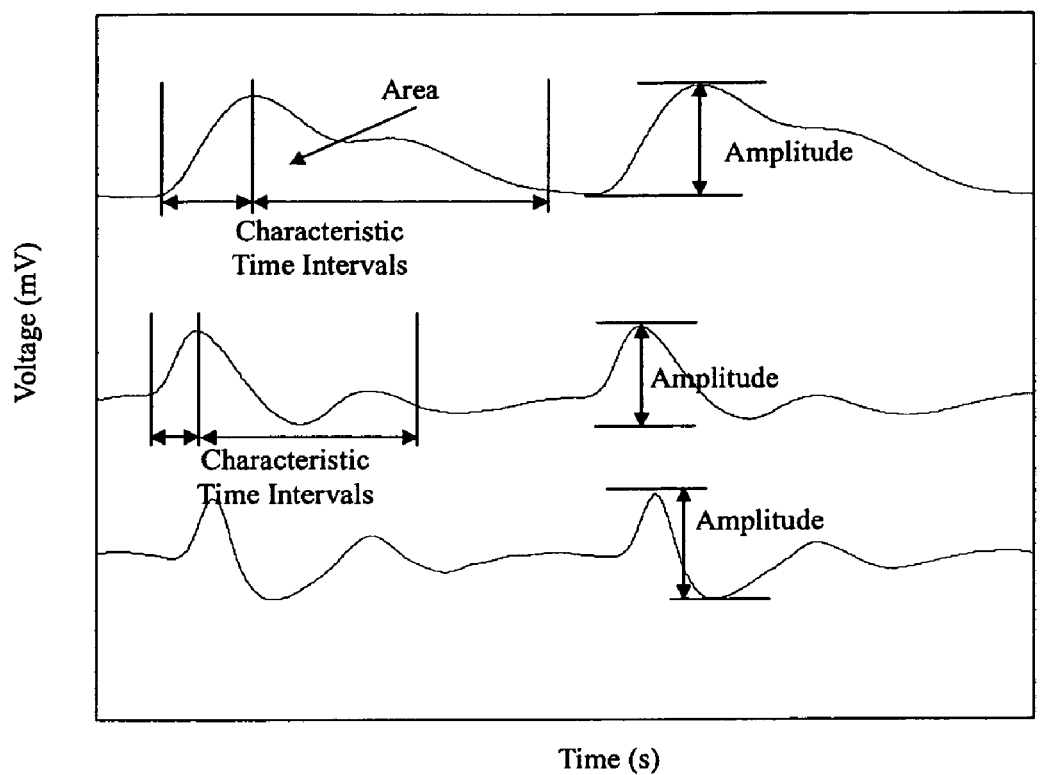
FIG. 3 shows characteristics of a photoplethysmographic signal.

In addition, other characteristics of the photoplethysmogram or other characteristics of a higher order moment or a higher order derivative of the photoplethysmogram, such as a magnitude, a characteristic time interval, a pulse area, can be used to measure the blood pressure. Therefore, the present invention could provide a noninvasive cuffless continuous measurement of arterial blood pressure without the use of electrocardiogram. FIG. 3 shows some of such characteristics. Since the invention does not intend to address how to measure the pulse transit time, the measurement of the pulse transit time will not be described in detail herein, and detailed information can be referred to those references listed herein.

Figure 2:
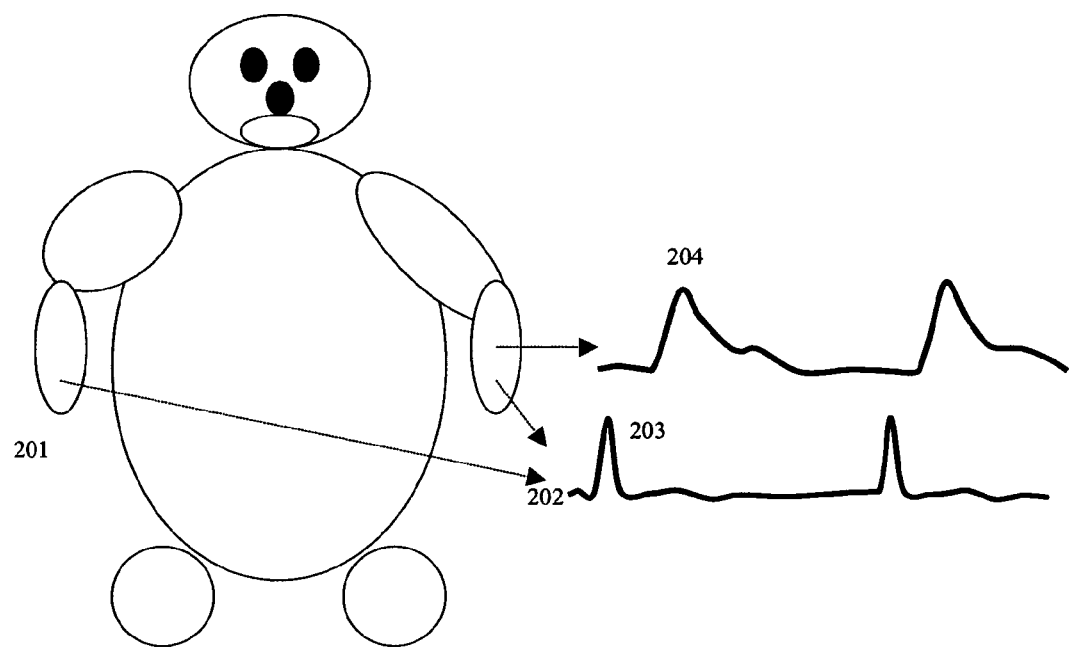
FIG. 2 shows locations where signals are collected.

FIG. 2 shows another embodiment of the invention. In this embodiment, photoplethysmogram and electrocardiogram come from human body. Photoplethysmogram 204 (peripheral artery) is from a finger of the left hand 202, and electrocardiogram 203 comes from a finger of both the left hand 202 and the right hand 201.

A sensor is preferably provided in the present invention that is positioned at a part of the subject's body (not shown) to obtain data related to the above characteristics. However, the data will be affected by a lot of factors related to the sensor.

Herein below is discussed in detail the effect of the contacting force between the sensor and the body, the ambient temperature, nervous activities, and cardiac output on the blood pressure.

Figure 4:
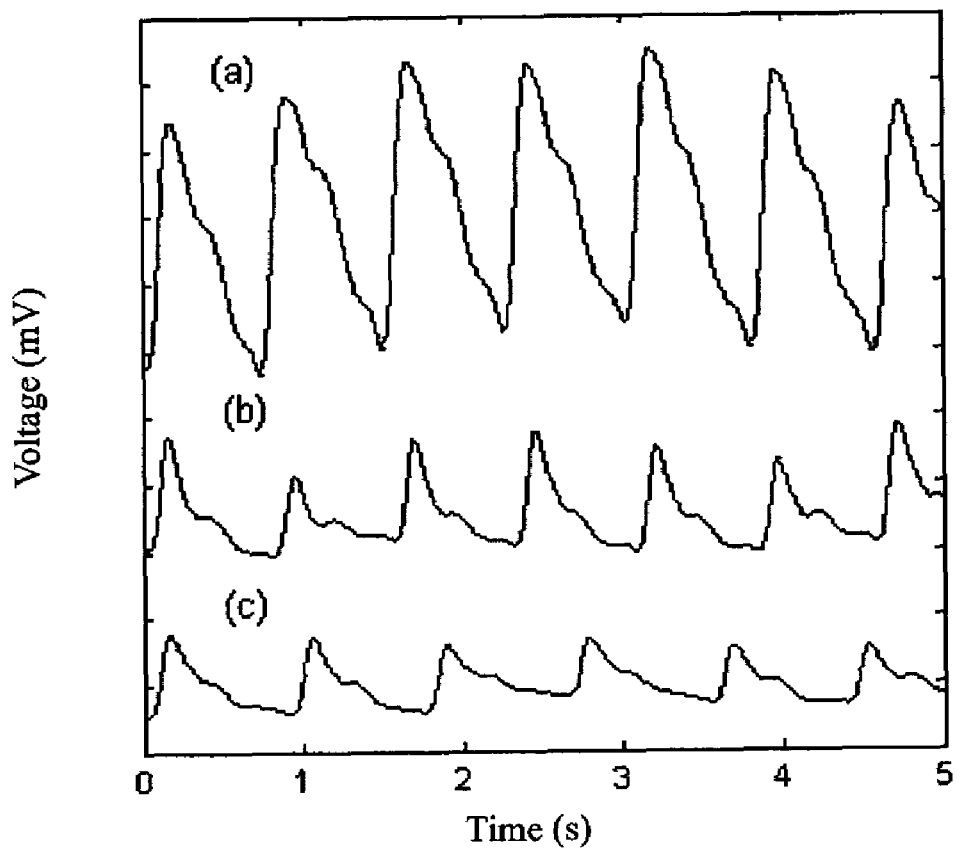
FIG. 4 illustrates photoplethysmogram waveforms at different contacting forces acting on a sensor.

As illustrated in FIGS. 4 ((a), (b), and (c)), the photoplethysmogram waveform changes with different contacting forces. As a result, the amplitude, and the time interval from the peak to the foot changes with various contacting forces. This affects the measured pulse transit time, and in turn influences the accuracy of the measured blood pressure. Therefore, the effect of the contacting force on the blood pressure measured by pulse transit time has to be counterbalanced. It is suggested in the invention that the amplitude of photoplethysmogram (Amp) be used to counterbalance the effect of the contacting force.

As illustrated in FIGS. 11(a) and 11(b), the photoplethysmogram waveform changes with the ambient temperature. The figures show that the position of the second peak of the pulse within a cardiac cycle changes at a different temperature. Hence, the pulse area will change with a variable ambient temperature, which will affect the blood pressure measured by the feature. Because the pulse area related signal characteristics could be used as an indicator of the temperature change, the invention suggests that pulse area related characteristics be used to counterbalance the effect of the ambient temperature.

FIG. 12 shows the pulse area of the photoplethysmogram related characteristics. The normalized pulse area is defined as (S1+S2)/(Amplitude×(T1+T2)) and the normalized falling area is defined as S2/(Amplitude×T2).

Figure 5:
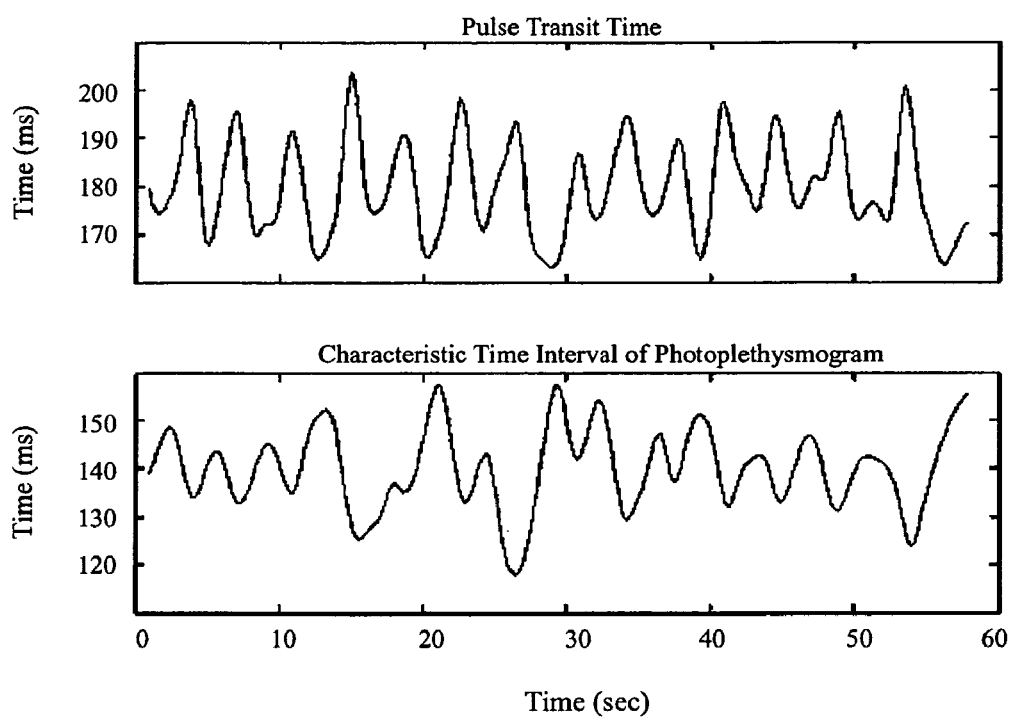
FIG. 5 shows a pulse transit time and a characteristic time interval of a photoplethysmographic signal in the time domain.
Figure 6:
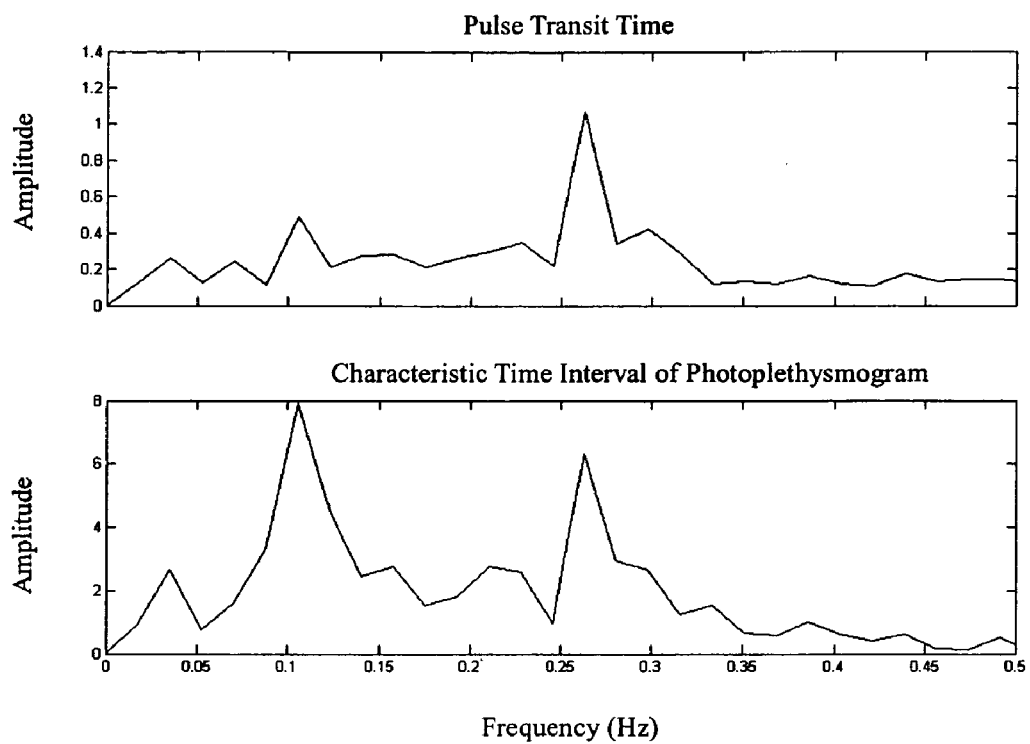
FIG. 6 shows a pulse transit time and a characteristic time interval of a photoplethysmogram in the frequency domain.

Measurement of the blood pressure by the pulse transit time which reflects the properties of the vascular system, is a simple and direct method. However, it is known that the blood pressure depends not only on the vascular properties, but also on the cardiac output and nervous activities. Investigation of the frequency spectrum of the blood pressure has shown that a low frequency component located at around 0.1 Hz is often noticed. The low frequency component reflects the fluctuation in the blood pressure, which is controlled by the nervous system. However, such a low frequency component is often not noticed on the frequency spectrum of the pulse transit time. FIG. 5 and FIG. 6 show a typical pulse transit time and a characteristic time interval of photoplethysmogram (Tc) in the time and frequency domain, respectively. A low frequency component is found in the frequency spectrum of the characteristic time interval of photoplethysmogram but not in that of the pulse transit time. Therefore, the invention suggests that a time interval on photoplethysmogram be used to counterbalance the effect of the nervous activities and/or cardiac output on the blood pressure measured by the feature.

In the invention, therefore the following equation is suggested to measure the blood pressure:

| | |
|---|---|
| $Psys = As/(Ts + Eps)^2 + Bs + Ins + Ds$ | (m1a) |
| $Pdia = Ad/(Td + Epd)^2 + Bd + Ind + Dd$ | (m1b) |
| where, | |
| $Eps = \Delta Amp \times Ep\_scon \times Wps$ | (m2a) |
| $Epd = \Delta Amp \times Ep\_dcon \times Wpd$ | (m2b) |
| $Ins = Tc \times In\_scon \times Wns$ | (m3a) |
| $Ind = Tc \times In\_dcon \times Wnd$ | (m3b) |
| $Ds = Wts \times \Delta S$ | (m4a) |
| $Dd = Wtd \times \Delta S$ | (m4b) |

Psys in Equation (m1a) and Pdia in Equation (m1b) are the systolic blood pressure (SBP) and the diastolic blood pressure (DBP), respectively. Ts and Td are the pulse transit time related to SBP and DBP, respectively.

As and Bs are SBP-related user-dependent coefficients, while Ad and Bd are similar coefficients related to DBP. As, Ad, Bs, and Bd are obtained from a database of the subject, or a calibration process which comprises: obtaining reference blood pressures Psys and Pdia of a subject using a conventional blood pressure measurement such as a standard sphygmomanometer; measuring pulse transit times Ts and Td corresponding to the reference blood pressures respectively; and determining values of As, Bs, Ad and Bd according to the equations below:

| | |
|---|---|
| $Psys = As/Ts^2 + Bs$ | (m5a) |
| $Pdia = Ad/Td^2 + Bd$ | (m5b) |

Eps and Epd are considered a first compensation term to counterbalance the effect of the contacting force acted on the sensor by the user on the estimated SBP and DBP respectively. Ins and Ind are considered a second compensation term to counterbalance the effect of the nervous activities and/or cardiac output on the estimated SBP and DBP respectively. And Ds and Dd are considered a third compensation term to counterbalance the effect of the ambient temperature. Amp and Tc are the amplitude and characteristic time interval of photoplethysmogram. $\Delta$Amp is the changes in the amplitude of the photoplethysmogram with respect to that obtained during the calibration. S is the pulse area of a photoplethysmogram-related characteristic. $\Delta$S is the change in the pulse area of the photoplethysmogram related characteristic with respect to that obtained during the calibration. Ep_scon, Ep_dcon, In_scon, and In_dcon are constants in each of the respective compensation terms. The constants can either be obtained from the calibration or determined as a percentage of As to Ad, or Bs to Bd.

Wps, Wpd, Wns, Wnd, Wts and Wtd are weighting factors in each of the respective compensation terms. The invention suggests that Wps and Wpd should be determined during the calibration as a ratio of the change in the pulse transit time to the change in the blood pressure. For Wns and Wnd, the invention suggests using a percentage difference in Tc with respect to that measured in the calibration. The details of the algorithm will be described below. By introducing a weighting factor in the compensation term, the degree of compensation can be applied more flexibly. The weighting factor, Wps, Wpd, Wns and Wnd, ranges from 0 to 1. When the weighting factor is set to 0, no counterbalancing effect will be applied. When the weighting factor is set to 1, the counterbalancing effect will be fully exercised. Wts and Wtd are in the range of 10 to 100.

Experimental results show that pulse transit time defined by different characteristic points on photoplethysmogram are affected by the contacting force to different extends. Therefore, the effect of the contacting force on the blood pressure measured from various pulse transit times is also different. Moreover, the pulse transit time of a healthy subject can range from 150 ms to 450 ms depending on the various definitions of the pulse transit time, i.e. from which a characteristic point on photoplethysmogram is defined to get a pulse transit time. In general, the effect of contacting force is often more noticeable for people with relatively lengthy pulse transit time than those who have relatively short pulse transit time. Based on this finding, there is a need to introduce a weighting factor so that the magnitude of the counterbalancing effect can be modulated.

Table 1 shows some weighting factors of Wps and Wpd, based on the ratio of the change in the pulse transit time and the change in the blood pressure obtained during the calibration. As shown in Table 1, the weighting factors Wps and Wpd are selected to be gradually increased with the ratio from 0 to 1.

TABLE 1

| Ratio R | 1 < R < 3 | 3 < R < 4 | 4 < R < 5 | R > 5 |
|---|---|---|---|---|
| Wps | Wps1 | Wps2 | Wps3 | Wps4 |
| Wpd | Wpd1 | Wpd2 | Wpd3 | Wpd4 |

Table 2 shows some weighting factors, Wns and Wnd, based on the calculated percentage difference. As shown in Table 2, the weighting factors Wns and Wnd increases with the percentage difference.

TABLE 2

| % Difference | ~10% | ~20% | ~35% | ~50% |
|---|---|---|---|---|
| Wns | Wns1 | Wns2 | Wns3 | Wns4 |
| Wnd | Wnd1 | Wnd2 | Wnd3 | Wnd4 |

Similar to As, Ad, Bs and Bd, Ep_scon, Ep_dcon, In_scon and In_dcon can be obtained from the calibration or by statistical analysis on a subjects' database. By pulse transit times, magnitudes and characteristic time intervals of photoplethysmogram at different contacting forces, and with reference to the blood pressure readings obtained from a standard sphygmomanometer, these coefficients can be characterized for each user. The information together with the weighting factors Wps and Wpd will be stored in a memory unit and used for measuring blood pressure in the next steps.

Figure 7:
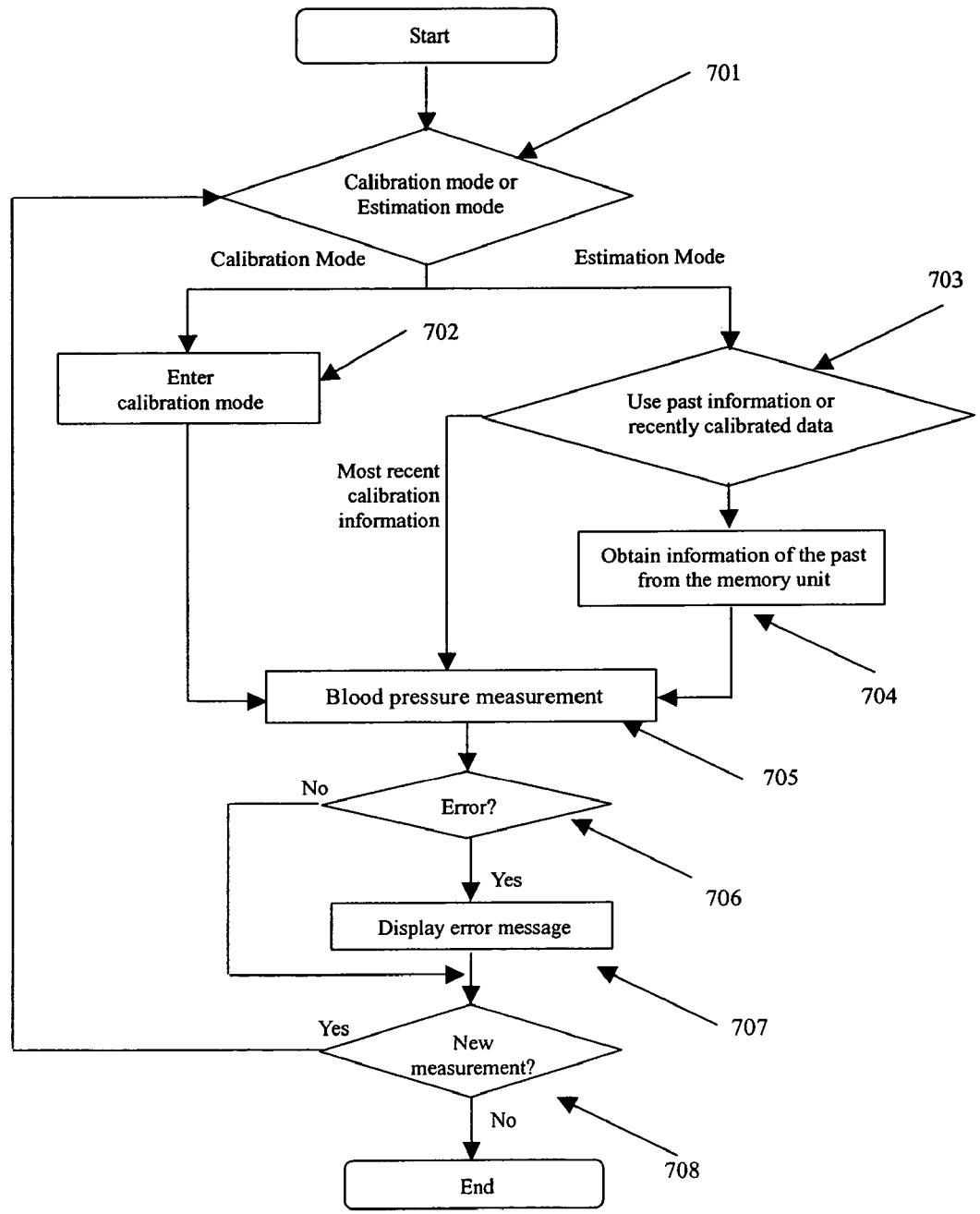
FIG. 7 is a flowchart to perform an embodiment of the invention.

FIG. 7 is a flowchart showing the blood pressure measurement of the invention. Since the measurement of the blood pressure by a pulse transit time requires a calibration procedure, user has to determine whether a new calibration is going to be carried out or calibration information recorded in the past is going to be used.

Now referring to FIG. 7, in step 701, if a subject (user) is called for a new calibration, the calibration mode is set in step 702, where the user-dependent coefficients As, Ad, Bs and Bd, as well as Ep_scon, Ep_dcon, In_scon, and In_dcon will be determined as described above.

If the measurement mode is selected, the user will be asked in step 703 whether the most recent calibration information is to be used or information recorded in the past is to be recalled from the memory unit. If the most recent calibration information is to be used, the algorithm directly enters the blood pressure mode in step 705. However, if the calibration information recorded in the past is to be used, the requested information has to be recalled from the memory unit in step 704, where user-dependent coefficients As, Bs, Ad, Bd, and all the calibrated coefficients and weighting factors in the compensation terms are loaded from the memory unit. After the information is loaded, the algorithm enters the next step 705, the systolic blood pressure and the diastolic blood pressure will be obtained and the resulted SBP and DBP can be transmitted to a display unit, which is described in detail in FIG. 8. After verified in step 706, either an error message will be displayed in step 707 if the blood pressure readings are not in a reasonable range or the user will be prompted to determine whether another measurement is needed in step 708. The procedure from step 701 to step 708 will be repeated until the user does not request further measurements.

Figure 8:
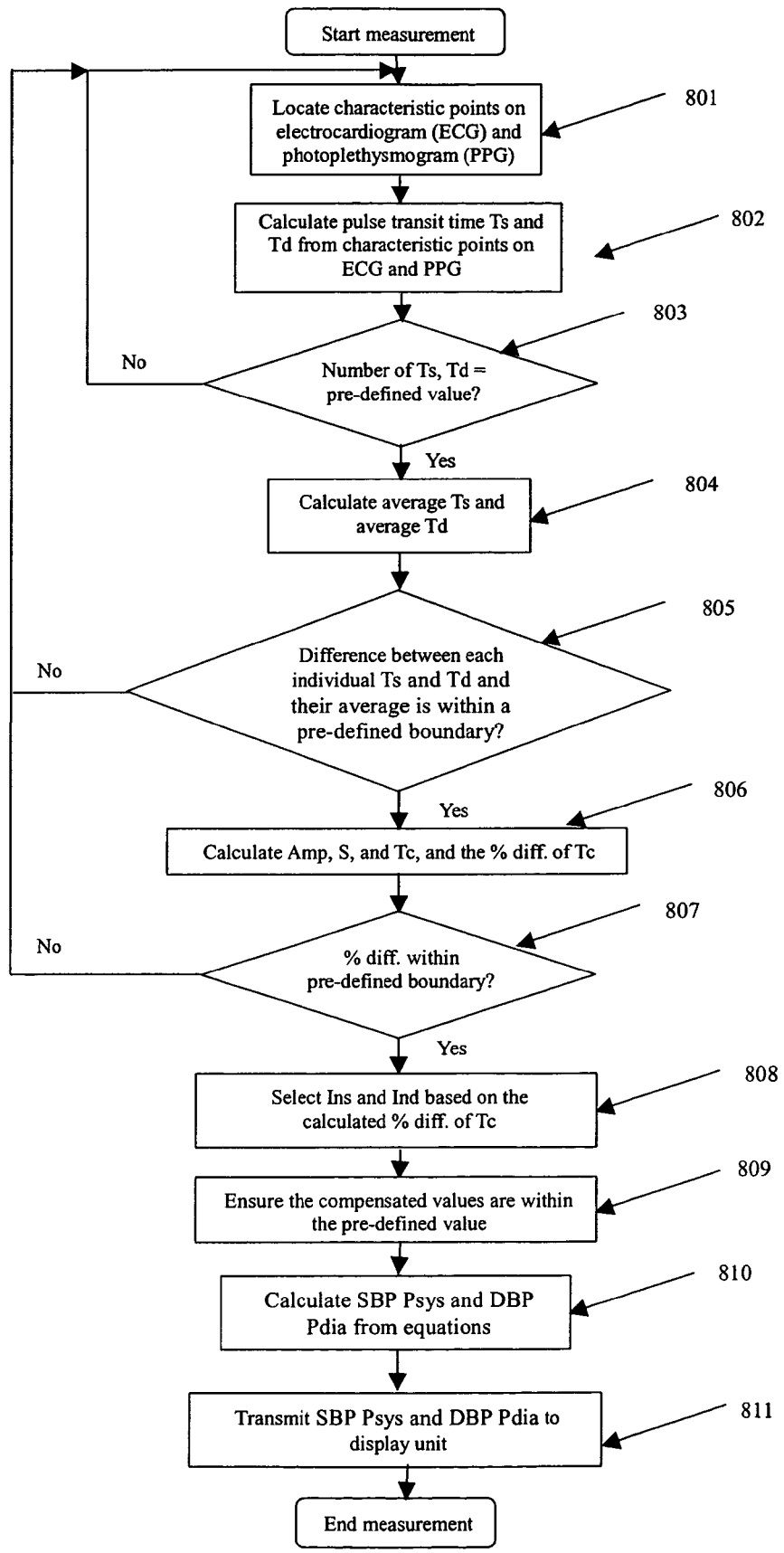
FIG. 8 is a flowchart showing the blood pressure measurement of the invention.

FIG. 8 is a flowchart showing detailed steps on the measurement of blood pressure in one embodiment according to the present invention. Step 801 and step 802 determine characteristic points on an electrocardiogram (ECG) and a photoplethysmogram (PPG) of a subject, and thereby calculate pulse transit times Ts and Td from the characteristic points identified on ECG and PPG. In the invention, the pulse transit times Ts and Td have to be within a boundary between Th_Tlow and Th_Thigh. Th_Tlow and Th_Thigh are preferably selected from 150 ms to 450 ms, respectively.

In the next step 803, a predetermined algorithm is used for checking whether the number of Ts and Td obtained have reached a pre-defined number P, e.g. P=5. Step 801 and step 802 are repeated until P pulse transit times are obtained to get an average pulse transit time Ts and Td in step 804, i.e., $$Ts = \frac{1}{P}\sum_{i=1}^{P} Ts_i \qquad (m6a)$$

$$Td = \frac{1}{P}\sum_{i=1}^{P} Td_i \qquad (m6b)$$

where, i is the index of a series of pulse transit times and $1 \leq i \leq P$.

In the following step 805, the algorithm ensures the difference between each pulse transit time Tsi and Tdi and the corresponding average Ts and average Td is within a predefined error boundary Th_Errlow and Th_Errhigh, e.g. Th_Errlow and Th_Errhigh are selected to be −15 ms and 15 ms respectively. For any $Ts_i$ and $Td_i$ that exceeds the boundary, step 801 to step 804 are repeated until the erroneous pulse transit time is replaced by one that satisfies the condition in step 805, i.e., $$Th\_Errlow < Ts - \{Ts_i\} < Th\_Errhigh \qquad (m7a)$$

$$Th\_Errlow < Td - \{Td_i\} < Th\_Errhigh \qquad (m7b)$$

The next step 806 obtains the characteristics of PPG in order to counterbalance the effect on the measurement of blood pressure raised by the various factors. The amplitude of PPG, Amp, a pulse area related characteristic, S, a characteristic time interval of PPG; Tc and a percentage difference thereof with respect to that measured during the calibration are obtained to counterbalance the effect of the contacting force, ambient temperature, nervous activities and/or cardiac output, respectively. The results are stored in the memory unit. The percentage difference of Tc can be calculated using the following equation:

$$\% \text{ Diff.} = \frac{Tc|_{during\ measurement} - Tc|_{during\ calibration}}{Tc|_{during\ calibration}} \quad (m8)$$

Step 807 determines whether the percentage difference exceeds a pre-defined boundary. If exceeded, e.g. by 50%, the system will display an error message and the complete measurement process has to be repeated starting from step 801.

Step 808 selects suitable values for the weighting factors Ins and Ind based on the percentage difference of Tc. Table 2 shows some weighting factors Wns and Wnd based on the calculated percentage difference, which can be used in the invention. As indicated in Table 2, the selected weighting factors Wns and Wnd increases with the percentage difference.

In addition, the values of Equations (m2a) and (m2b) must be within a predefined boundary, between Th_Eplow and Th_Ephigh. It is suggested but not limited to in the invention that ThEplow and Th_Ephigh be −20 ms and 50 ms, respectively. The values of Ins in Equation (m3a) and Ind in Equation (m3b) must be within a predefined boundary, between Th_Inlow and Th_Inhigh, where Th_Inlow and Th_Inhigh are suggested but not limited to −10 mmHg and 15 mmHg, respectively. Therefore, the various compensation terms will be tested against the pre-defined boundaries in step 809. A compensation term is limited to the pre-defined boundary if the measured value exceeds the boundary.

Step 810 employs the measured values Ts, Td, Amp, S, and Tc, the weighting factors in the compensation terms, as well as the stored user-dependent information As, Ad, Bs, Bd, Ep_scon, In_scon, Ep_dcon, In_dcon, Wps, Wpd, and the corresponding Amp and Tc recorded during the calibration, and the weighting factors Wns and Wnd obtained based on the percentage difference of As, Bs. Ad, Bd, to Equations (m1a) and (m1b) to obtain measured SBP Psys and DBP Pdia. After that, the resulted SBP and DBP can be transmitted to a display unit in step 811. Since the invention takes into account and counterbalances the effect of various factors on the blood pressure, more accurate blood pressure are resulted.

Those skilled in the art should understand that the above embodiments are only utilized to describe the invention. There are many modifications and variations to the invention without departing the spirit of the invention. For example, the algorithm can be modified or replaced based on the spirit of the invention. It is understood that in stead of the Equations (m1a) and (m1b), any of the following equivalent equations can be possibly used to measure the blood pressure:

$$Psys = As' \times \ln(Ts + Eps)^{n1} + Bs' + Ins^{\alpha 1} + Ds^{\beta 1} \quad (m1a')$$

$$Pdia = Ad' \times \ln Td + Epd)^{n2} + Bd' + Ind^{\alpha 2} + Dd^{\beta 2} \quad (m1b')$$

and $$Psys = As'' \times Ins^{\alpha 1}/(Ts \times Eps)^{n1} + Bs'' + Ds^{\beta 1} \quad (m1a'')$$

$$Pdia = Ad'' \times Ind^{\alpha 2}/(Td \times Epd)^{n2} + Bd'' + Dd^{\beta 2} \quad (m1b'')$$

where, definitions of Ts, Td, Eps, and Epd are the same as those in Equations (m1a) and (m1b); and As', Bs', Ad' and Bd', and As'', Bs'', Ad'' and Bd'' that correspond to As, Bs, Ad, and Bd respectively, can be obtained from the calibration or by statistical analysis on a subjects' database.

Although Equations (m1a) and (m1b), (m1a') and (m1b'), as well as (m1a'') and (m1b'') are represented differently, those skilled in the art can select the appropriate equations and set of constants As, Bs, Ad, and Bd, As', Bs', Ad', and Bd', or As'', Bs'', Ad'', and Bd'' to obtain the most accurate blood pressure.

It is also noted that though the invention has suggested compensating and counterbalancing the effect of the contacting force, ambient temperature, nervous activities, and cardiac output on the blood pressure, it is obvious for those skilled in the art to apply the compensation with one or more compensation terms, for example, only counterbalancing the effect of the contacting force. Moreover, the overall compensation can be a summation or a product of each individual compensation term. For example, it is possible to introduce Eps×Ins and Epd×Ind in the blood pressure equation.

In the invention, it is also possible to calculate the percentage difference of Tc as:

$$\% \text{ Diff.} = \frac{Tc|_{during\ calibration}}{Tc|_{during\ measurement} - Tc|_{during\ calibration}}$$

It is appreciated that the scope of the invention is defined in the appended claims and should not be restricted by the description discussed in the summary and/or the detailed description of the preferred embodiments.

The invention claimed is:

1. A method for measuring an arterial blood pressure of a subject, comprising:
    a) detecting pulse-wave-related signals of the subject with a sensor;
    b) extracting a feature from the signals;
    c) determining factors that can affect the feature; and
    d) determining the arterial blood pressure based on the feature with an automatic compensation for the factors,
  wherein the feature is a pulse transit time and the factors comprise a contacting force to the sensor, nervous activities and/or cardiac outputs of the subject, and ambient temperatures,
  and wherein the step d) further comprises:
    1) obtaining coefficients from a calibration process;
    2) counterbalancing effects of the factors on the pulse transit time with a first compensation term;
    3) determining an estimated value of the arterial blood pressure according to the result of the counterbalancing;
    4) counterbalancing the effects of the nervous activities and/or cardiac outputs on the estimated value with a second compensation term; and
    5) counterbalancing the effects of the ambient temperatures on the estimated value of the arterial blood pressure with a third compensation term.

2. The method of claim 1, wherein the sensor is positioned on the subject.

3. The method of claim 2, wherein the pulse-wave-related signals comprise an electrocardiographic (ECG) signal and a photoplethysmographic (PPG) signal.

4. The method of claim 3, wherein the pulse transit time is a time interval between a first characteristic point at the electrocardiographic signal, and a second characteristic point at the photoplethysmographic signal of the subject.

5. The method of claim 4, wherein the second characteristic point is at a peak or a foot of the photoplethysmographic signal.

6. The method of claim 4, wherein the pulse transit time is a time interval between a first characteristic point at an R wave of the electrocardiographic signal and a second characteristic point at the photoplethysmographic signal of the subject.

7. The method of claim 6, wherein the first characteristic point is at the peak of the R wave.

8. The method of claim 4, wherein the pulse transit time is a time interval between a first characteristic point at the electrocardiographic signal and a second characteristic point at photoplethysmographic signal within a cardiac cycle.

9. The method of claim 1, wherein the step d4) is performed in accordance with a non-linear function.

10. The method of claim 9, wherein the blood pressure is determined by one group of following equations:

$$Psys = As/(Ts+Tcs)^{n1} + Bs + Cs^{\alpha 1} + Ds^{\beta 1}$$

$$Pdia = Ad/(Td+Tcd)^{n2} + Bd + Cd^{\alpha 2} + Dd^{\beta 2};$$

$$Psys = As' \times \ln(Ts+Tcs)^{n1} + Bs' + Cs^{\alpha 1} + Ds^{\beta 1}$$

$$Pdia = Ad' \times \ln(Td+Tcd)^{n2} + Bd' + Cd^{\alpha 2} + Dd^{\beta 2}; \text{ and}$$

$$Psys = As'' \times Cs^{\alpha 1} \times Ds^{\beta 1}/(Ts \times Tcs)^{n1} + Bs''$$

$$Pdia = Ad'' \times Cd^{\alpha 2} \times Dd^{\beta 2}/(Td \times Tcd)^{n2} + Bd'',$$

wherein Psys and Pdia are an estimated systolic blood pressure and an estimated diastolic blood pressure, respectively; Ts and Td are the pulse transit time used to measure the systolic blood pressure and the diastolic blood pressure, respectively; As, Bs, Ad, Bd, As', Bs', Ad', Bd', As", Bs", Ad", and Bd" are coefficients used in step d1), which are predefined or obtained from the calibration process; Tcs and Tcd are the first compensation terms for counterbalancing effects of the contacting force on the pulse transit times Ts and Td, respectively; n1 and n2 are a power of Ts and a power of Td, respectively, where $0 < n1, n2 \leq 3$; Cs and Cd are the second compensation terms for counterbalancing the effects of nervous activities and/or cardiac outputs on the estimation of the systolic and diastolic blood pressure, respectively; $\alpha 1$ and $\alpha 2$ are a power of Cs and a power of Cd, respectively, where $0 \leq \alpha 1, \alpha 2 \leq 2$; Ds and Dd are the third compensation terms for counterbalancing the effects of the ambient temperatures on the estimation of the systolic and/or diastolic blood pressure, respectively; and $\beta 1$ and $\beta 2$ are a power of Ds and a power of Dd, respectively, where $0 \leq \beta 1, \beta 2 \leq 2$.

11. The method of claim 10, wherein the pulse-wave-related signals comprise photoplethysmographic signals.

12. The method of claim 11, wherein each of the compensation terms further comprises at least one photoplethysmographic signal characteristic, and at least one weighting factor, and optionally at least one calibration constant.

13. The method of claim 12, wherein the photoplethysmographic signal characteristic comprises one of a magnitude, a characteristic time interval, a pulse area, and a higher order moment.

14. The method of claim 13, wherein Tcs and Tcd are determined by the magnitude, a first calibration constant and a first weighting factor.

15. The method of claim 14, wherein the first weighting factor is determined by a ratio of a change of the pulse transit time to a change of the blood pressure.

16. The method of claim 13, wherein Cs and Cd are determined by a characteristic time interval of the photoplethysmographic signal, a second calibration constant and a second weighting factor.

17. The method of claim 16, wherein the characteristic time interval includes a time interval from the bottom of the photoplethysmographic signal to a characteristic point of a peak of the photoplethysmographic signal within a cardiac cycle, or a time interval from the peak of the photoplethysmographic signal to a characteristic point of a bottom of the photoplethysmographic signal at the next cardiac cycle.

18. The method of claim 16, wherein the second weighting factor is determined by the characteristic time interval of the photoplethysmographic signal and a percentage difference in the characteristic time interval obtained during the measurement of the blood pressure as compared to that obtained during the calibration.

19. The method of claim 18, wherein the percentage difference is:

$$\% \text{ Diff.} = \frac{CTI |_{during\ measurement} - CTI |_{during\ calibration}}{CTI |_{during\ calibration}}, \text{ or,}$$

$$\% \text{ Diff.} = \frac{CTI |_{during\ calibration}}{CTI |_{during\ measurement} - CTI |_{during\ calibration}}$$

where $CTI |_{during\ measurement}$ is the characteristic time interval obtained during the measurement, and $CTI |_{during\ calibration}$ is the characteristic time interval obtained during the calibration.

20. The method of claim 18, wherein the second calibration constant is obtained from a ratio of As to Bs for the estimation of the systolic blood pressure, and that of Ad to Bd for the estimation of the diastolic blood pressure.

21. The method of claim 13, wherein Ds and Dd are determined by a pulse wave area of the photoplethysmographic signal, a third calibration constant and a third weighting factor.

22. The method of claim 21, wherein the third weighting factor is a constant ranging from 10 to 100.

23. The method of claim 10, wherein Ts and Td are respectively obtained by the following equations:

$$Ts = \frac{1}{P}\sum_{i=1}^{P} Ts_i, \text{ and, } Td = \frac{1}{P}\sum_{i=1}^{P} Td_i$$

where i is an index of a series of pulse transit times and $1 \leq i \leq P$.

24. The method of claim 23, wherein the difference between Ts and $Ts_i$, or that between Td and $Td_i$, is within a boundary defined below:

$$Th\_Errlow < Ts - \{Ts_i\} < Th\_Errhigh; \text{ and}$$

$$Th\_Errlow < Td - \{Td_i\} < Th\_Errhigh$$

where Th_Errhigh and Th_Errlow are a pre-defined boundary.

* * * * *